(12) United States Patent
Lee et al.

(10) Patent No.: US 11,525,801 B2
(45) Date of Patent: Dec. 13, 2022

(54) STRIP STRUCTURE FOR MEASURING POTASSIUM IONS

(71) Applicant: THEDONEE INC., Suwon-si (KR)

(72) Inventors: Kang Won Lee, Suwon-si (KR); Kyung Hwan Moon, Suwon-si (KR); Sun Mi Lee, Seoul (KR)

(73) Assignee: THEDONEE INC., Suwon-si (KR)

( * ) Notice: Subject to any disclaimer, the term of this patent is extended or adjusted under 35 U.S.C. 154(b) by 447 days.

(21) Appl. No.: 16/707,263

(22) Filed: Dec. 9, 2019

(65) Prior Publication Data

US 2020/0191741 A1 Jun. 18, 2020

(30) Foreign Application Priority Data

Dec. 17, 2018 (KR) .................. 10-2018-0163318

(51) Int. Cl.
*G01N 27/333* (2006.01)
*G01N 33/52* (2006.01)
*G01N 33/84* (2006.01)
*B01D 71/10* (2006.01)

(52) U.S. Cl.
CPC ......... *G01N 27/3335* (2013.01); *B01D 71/10* (2013.01); *G01N 33/526* (2013.01); *G01N 33/84* (2013.01)

(58) Field of Classification Search
CPC ............ G01N 33/5438; G01N 27/4145; H01L 51/0562; H01L 51/0048; H01L 27/283; H01L 51/0541
See application file for complete search history.

(56) References Cited

U.S. PATENT DOCUMENTS

| 3,753,887 | A | * | 8/1973 | Kedem | ............. | G01N 27/3335 |
| | | | | | | 204/417 |
| 6,663,756 | B2 | | 12/2003 | Lee et al. | | |
| 8,337,683 | B2 | | 12/2012 | Choi et al. | | |
| 2004/0016642 | A1 | | 1/2004 | Miyazaki et al. | | |

(Continued)

FOREIGN PATENT DOCUMENTS

| CN | 102636532 B | 7/2014 |
| JP | H04-339251 A | 11/1992 |

(Continued)

OTHER PUBLICATIONS

Notification of Reason for Refusal dated Oct. 13, 2020 in Japanese Patent Application No. 2019-225348, filed Dec. 13, 2019, 8 pages.

(Continued)

*Primary Examiner* — Dennis White
(74) *Attorney, Agent, or Firm* — Kilpatrick Townsend & Stockton LLP (57) ABSTRACT

A strip structure for measuring potassium ions includes: a strip having an inner space for receiving a solution therein and being formed in a plate shape; an inlet formed in the strip and capable of injecting a solution into the inner space of the strip; a potassium ion selective membrane arranged in the inner space and capable of permeating potassium ions of the solution; and a first working electrode extending in a strip shape, wherein one side of the first working electrode is arranged inside the potassium ion selective membrane and the other side of the first working electrode is on a surface of the strip.

9 Claims, 9 Drawing Sheets

(56) References Cited

U.S. PATENT DOCUMENTS

| | | |
|---|---|---|
| 2010/0147688 A1 | 6/2010 | Hadidy |
| 2013/0168247 A1* | 7/2013 | Iwamoto ............... G01N 27/333 |
| | | 204/417 |
| 2014/0105788 A1 | 4/2014 | Iwamoto et al. |
| 2018/0143156 A1 | 5/2018 | Peng et al. |
| 2018/0164243 A1 | 6/2018 | Noumi et al. |

FOREIGN PATENT DOCUMENTS

| | | |
|---|---|---|
| JP | 2001-159618 A | 6/2001 |
| JP | 2002-181757 A | 6/2002 |
| JP | 2013-137218 A | 7/2013 |
| KR | 10-2009-0011557 A | 2/2009 |
| KR | 10-2018-0008486 A | 1/2018 |
| WO | 02/097419 A1 | 12/2002 |

OTHER PUBLICATIONS

Extended European Search Report dated May 14, 2020 in European Patent Application No. 19215501.8, filed Dec. 12, 2019, 9 pages.
Communication from European Patent Office for EP 19 215 501.8 dated Aug. 26, 2022, 6 pages.

* cited by examiner

STRIP STRUCTURE FOR MEASURING POTASSIUM IONS

CROSS-REFERENCE TO RELATED APPLICATION

This application claims the benefit of Korean Patent Application No. 10-2018-0163318, filed on Dec. 17, 2018, in the Korean Intellectual Property Office, the disclosure of which is incorporated herein in its entirety by reference.

BACKGROUND

1. Field

One or more embodiments relate to a strip structure for measuring potassium ions, and more particularly, to a strip structure for potassium ion measurement capable of simply measuring potassium ions in the body in a short time by using a strip including a potassium ion selective membrane and a working electrode.

2. Description of the Related Art

Potassium, together with sodium, is an important electrolyte in the body, and potassium acts in conjunction with sodium to control the body's water and acid and alkaline balance. The balance of potassium and sodium affects maintenance of normal blood pressure, muscle contraction and relaxation, and the like, and such potassium balance is regulated in the kidney.

If the potassium concentration in the body is abnormal, it may adversely affect the body. Therefore, the potassium concentration in the body is measured to determine whether the potassium concentration is abnormal. The potassium concentration in the body is measured in the hospital through a blood test, an electrocardiogram examination, and so on. According to a method of measuring the potassium concentration in the body, first, a potassium-containing solution is filtered through a membrane for filtering ions, and the concentration of potassium ions is measured by measuring potential (V).

The potassium concentration in the body is measured for the purpose of research or treatment. Since a conventional potassium concentration measuring device is large, the conventional potassium concentration measuring device may not be directly used by patients to measure potassium concentration. In addition, the conventional potassium concentration measuring device requires an excess amount of blood or solution, and the accuracy is lowered because, after use, a membrane is washed with water and reused.

In some patients, it is necessary to measure the potassium concentration at all times. However, since the conventional potassium concentration measuring method requires a blood test, an electrocardiogram examination, and so on, it takes a lot of time and money. Also, it is difficult for the patient to constantly measure the potassium concentration due to the non-portable potassium concentration measuring device.

In particular, patients with kidney disease need to constantly measure the potassium concentration in the body because the regulation of potassium concentration in the body is very important. However, it is difficult to measure the potassium concentration in patients with kidney disease at all times by the conventional potassium concentration measuring method, and thus it is difficult to manage potassium concentration in the patients with kidney disease.

SUMMARY

One or more embodiments include a strip structure for potassium ion measurement capable of simply measuring potassium ions in the body in a short time by using a strip including a potassium ion selective membrane and a working electrode.

Additional aspects will be set forth in part in the description which follows and, in part, will be apparent from the description, or may be learned by practice of the presented embodiments.

According to one or more embodiments, a strip structure for measuring potassium ions includes: a strip having an inner space for receiving a solution therein and being formed in a plate shape; an inlet formed in the strip and capable of injecting a solution into the inner space of the strip; a potassium ion selective membrane arranged in the inner space and capable of permeating potassium ions of the solution; and a first working electrode extending in a strip shape, wherein one side of the first working electrode is arranged inside the potassium ion selective membrane and the other side of the first working electrode is on a surface of the strip.

The strip structure may further include: a measuring device comprising a reference electrode and an inlet into which the strip is inserted, wherein the measuring device may be separated from the strip and measures potassium ions by inserting the strip into the inlet of the measuring device.

The first working electrode may extend upward and obliquely with respect to a direction in which the strip extends in a longitudinal direction.

The strip structure may further include: a blood filter membrane arranged in the inner space and capable of removing foreign matter of the solution; and a second working electrode extending in a strip shape, wherein one side of the second working electrode may be arranged inside the potassium ion selective membrane and the other side of the second working electrode is in the surface of the strip, wherein the blood filter membrane may be arranged between the inlet and the potassium ion selective membrane, and one side of the second working electrode may be between the blood filter membrane and the potassium ion selective membrane.

The second working electrode may extend upward and obliquely with respect to a direction in which the strip extends in a longitudinal direction.

The inlet may include a capillary having a diameter less than a diameter of the inner space.

The inlet may include a plurality of capillaries.

The potassium ion selective membrane may include cellulose acetate.

The strip may include an insertion hole arranged in the surface of the strip and communicating with the inner space, and the reference electrode of the measuring device may be inserted into the insertion hole when the strip is inserted into the measuring device.

The strip structure may further include: a reference electrode extending in a strip shape, wherein one side of the reference electrode may be arranged outside the potassium ion selective membrane and the other side of the reference electrode is in the surface of the strip.

A gap between the first working electrode and the potassium ion selective membrane may be filled with an electrolytic material.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

One or more embodiments relate to a strip structure for potassium ion measurement capable of simply measuring potassium ions in the body in a short time by using a strip including a potassium ion selective membrane and a working electrode. Hereinafter, embodiments of the present disclosure will be described in detail with reference to the accompanying drawings.

A solution 10 that may be used in the embodiments may be blood or urine. However, the present disclosure is not limited thereto, and the solution 10 may be a specific solution containing potassium.

Figure 1:
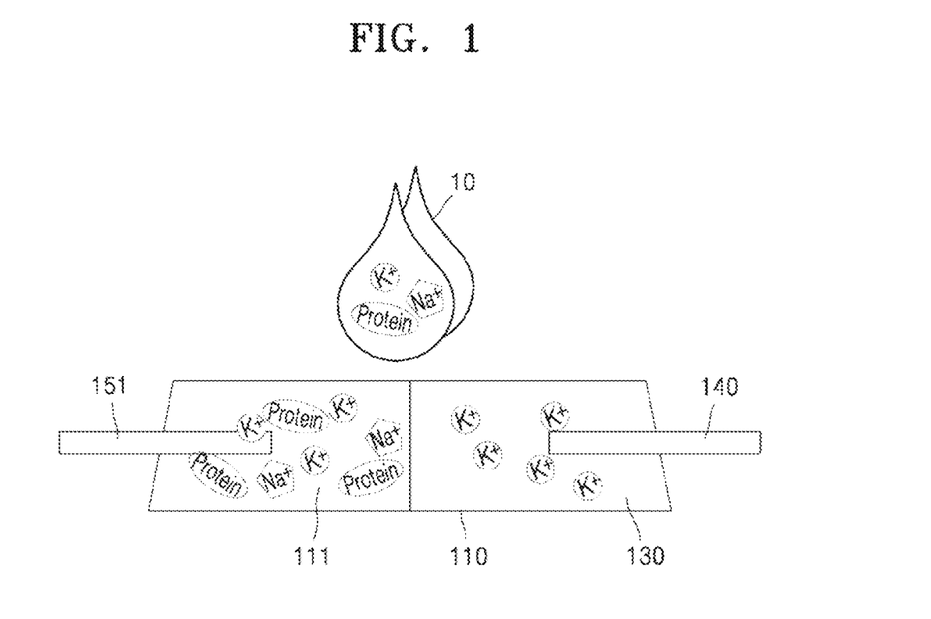
FIG. 1 is a view of a method of measuring the concentration of potassium ions through a reference electrode and a working electrode.

FIG. 1 is a view of a method of measuring the concentration of potassium ions through a reference electrode and a working electrode. Referring to FIG. 1, when the solution 10 containing potassium ions is sufficiently dropped on a strip 110, the solution 10 enters a potassium ion selective permeation membrane 130 for a certain period of time, whereby only potassium ions may be selectively filtered.

Here, the potassium ion selective membrane 130 covers a working electrode 140, and the working electrode 140 is brought into contact with the solution 10 in which only potassium ions are selectively filtered. A reference electrode 151 is located near the potassium ion selective membrane 130 and is in contact with the solution 10 before being filtered through the potassium ion selective permeation membrane 130.

By using the potassium ion selective membrane 130 as described above, potential (V) varies depending on the concentration of potassium in the reference electrode 151 and the working electrode 140, and the concentration of potassium ions of the solution 10 may be measured by detecting the potential (V).

FIG. 1 schematically shows a method of measuring the concentration of potassium ions through the strip 110 and the reference electrode 151 including the working electrode 140 and the potassium ion selective membrane 130. According to an embodiment, the reference electrode 151 may be included in a measuring device 150, which is separated from the strip 110. Also, the reference electrode 151 may be included in the strip 110 if necessary. Hereinafter, embodiments of the present disclosure will be described in detail Referring to FIGS. 2 and 3, a strip structure for measuring potassium ions according to an embodiment may include the strip 110, an inlet 120, the potassium ion selective membrane 130, and the first working electrode 140.

Figure 2:
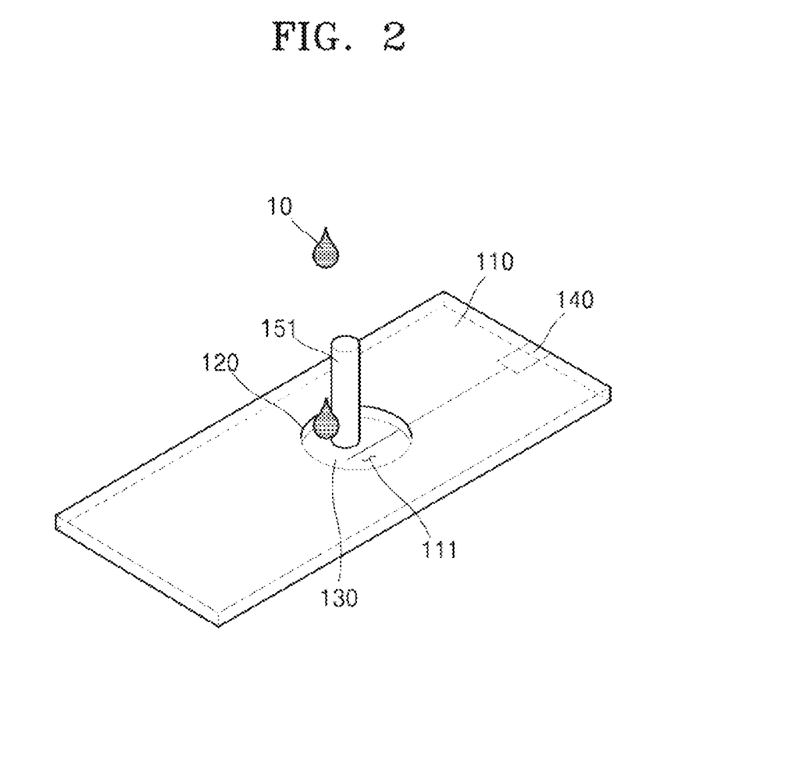
FIG. 2 is a perspective view of a strip according to an embodiment.

Referring to FIG. 2, the strip 110 has an inner space 111 for receiving the solution 10 therein, and may be formed in a plate shape. The strip 110 may include polydimethylsiloxane (PDMS), which may be a disposable strip.

The strip 110 has the inner space 111 for receiving the solution 10 therein, and the potassium ion selective membrane 130 and the first working electrode 140 may be arranged in the inner space 111. When the solution 10 is dropped into the inner space 111, the solution 10 may be brought into contact with the first working electrode 140 after passing through the potassium ion selective membrane 130 in the inner space 111.

As will be described later below, the strip 110 may be inserted into the measuring device 150 and used for disposable use. Since the strip 110 is used for disposable use, it is possible to easily measure the concentration of potassium ions in the body and the accuracy may be improved because it is not reused.

The inlet 120 is formed in the strip 110 and is an entrance through which the solution 10 may be injected into the inner space 111 of the strip 110. The inlet 120 is communicated with the inner space 111, and when the solution 10 is injected through the inlet 120, the solution 10 may be injected into the inner space 111 through the inlet 120.

The inlet 120 may be a circular hole in an upper surface of the strip 110, but is not limited thereto. The inlet 120 may be arranged at various points as long as the inlet 120 can communicate with the inner space 111 and inject the solution 10 into the inner space 111. As will be described later below, the inlet 120 may be arranged on a side surface of the strip 110 and the inlet 120 may be a thin tube (capillary) having a diameter less than a diameter of the inner space 111 to utilize a capillary phenomenon.

The potassium ion selective membrane 130 is arranged in the inner space 111 and is capable of permeating potassium ions of the solution 10. The potassium ion selective membrane 130 is selectively permeable to potassium ions. The solution 10 injected through the inlet 120 is injected into the inner space 111 and passes through the potassium ion selective membrane 130.

The potassium ion selective membrane 130 may include cellulose acetate and may be made of a natural polymer-derived material. In more detail, cellulose acetate including valinomycin may be used. As described above, the strip 110 may be discarded after one use. Therefore, the potassium ion selective membrane 130 is preferably made of a natural material which is inexpensive and is decomposed quickly when it is discarded.

Figure 4:
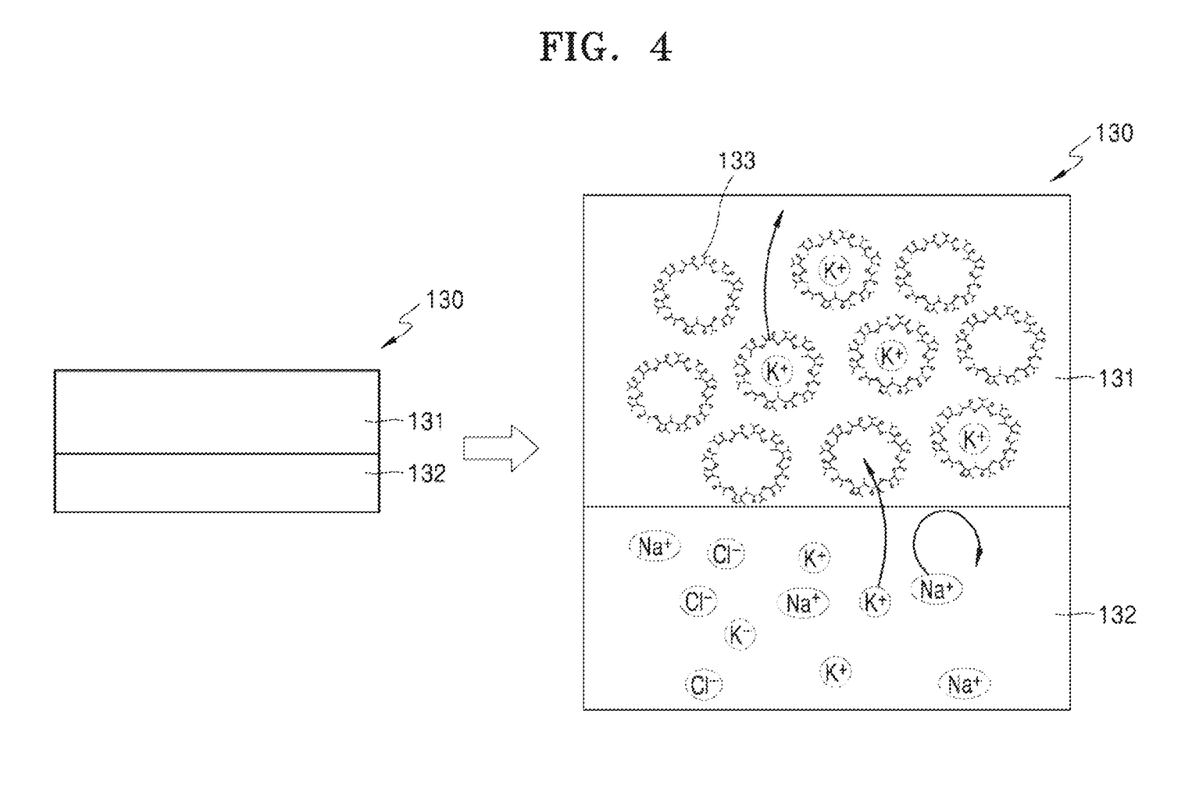
FIG. 4 is a view of a potassium ion selective membrane according to an embodiment.

Referring to FIG. 4, the potassium ion selective membrane 130 may also be a double membrane. In more detail, the potassium ion selective membrane 130 may include a protective membrane 132 and a membrane 131.

The protective membrane 132 is formed with pores through a method such as electrospinning and is capable of filtering the solution 10 through the pores. The protective membrane 132 protects the potassium ion selective membrane 130 and is an area where the solution 10 containing potassium ions may be collected.

The membrane 131 includes valinomycin 133 as a substance with ion transport ability and may selectively filter only potassium ions in the protective membrane 132 through the valinomycin 133. That is, in the solution 10 containing potassium in the protective membrane 132, only potassium ions are selectively filtered by the membrane 131, thereby separating potassium ions. The membrane 131 may be a PVC membrane or may be a cellulose acetate membrane.

The first working electrode 140 extends in a strip shape, wherein one side of the first working electrode 140 is arranged inside the potassium ion selective membrane 130 and the other side of the first working electrode 140 is on a surface of the strip 110. The inside of the potassium ion selective membrane 130 refers to an area where the solution 10 is permeated through the potassium ion selective membrane 130.

Figure 3:
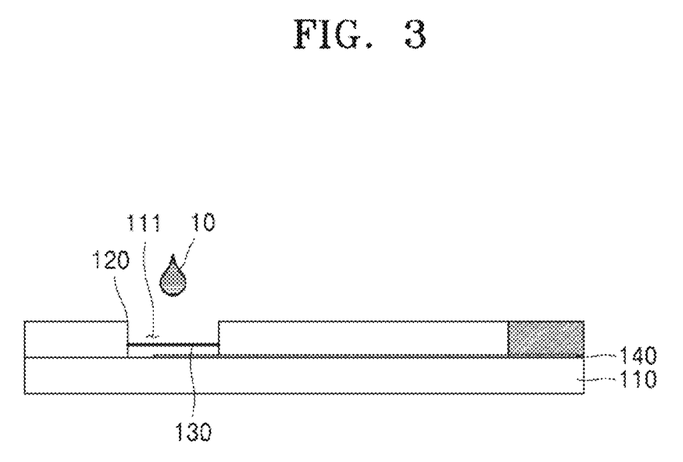
FIG. 3 is an internal cross-sectional view of a strip according to an embodiment.

In more detail, referring to FIG. 3, the direction toward the inlet 120 may be an outer side and the opposite direction may be an inner side with the potassium ion selective membrane 130 provided in the inner space 111 as a center. One side of the first working electrode 140 is arranged inside the potassium ion selective membrane 130, and is brought into contact with a portion that selectively permeates only potassium ions.

The first working electrode 140 may extend in a strip shape and may extend from the inside of the potassium ion selective membrane 130 to the surface of the strip 110. As shown in FIG. 3, the other side of the first working electrode 140 is preferably arranged in the surface of the strip 110 so as to be exposed to the outside of the strip 110.

As will be described later below, the strip 110 is inserted into the measuring device 150 so that the measuring device 150 may measure potassium ions using the reference electrode 151 included in the measuring device 150. Since the concentration of potassium ions may be measured only when the first working electrode 140 is brought into contact with the measuring device 150 when the strip 110 is inserted into the measuring device 150, the first working electrode 140 needs to be exposed to the outside of the strip 110. Therefore, the other side of the first working electrode 140 is preferably arranged in the surface of the strip 110.

Figure 5:
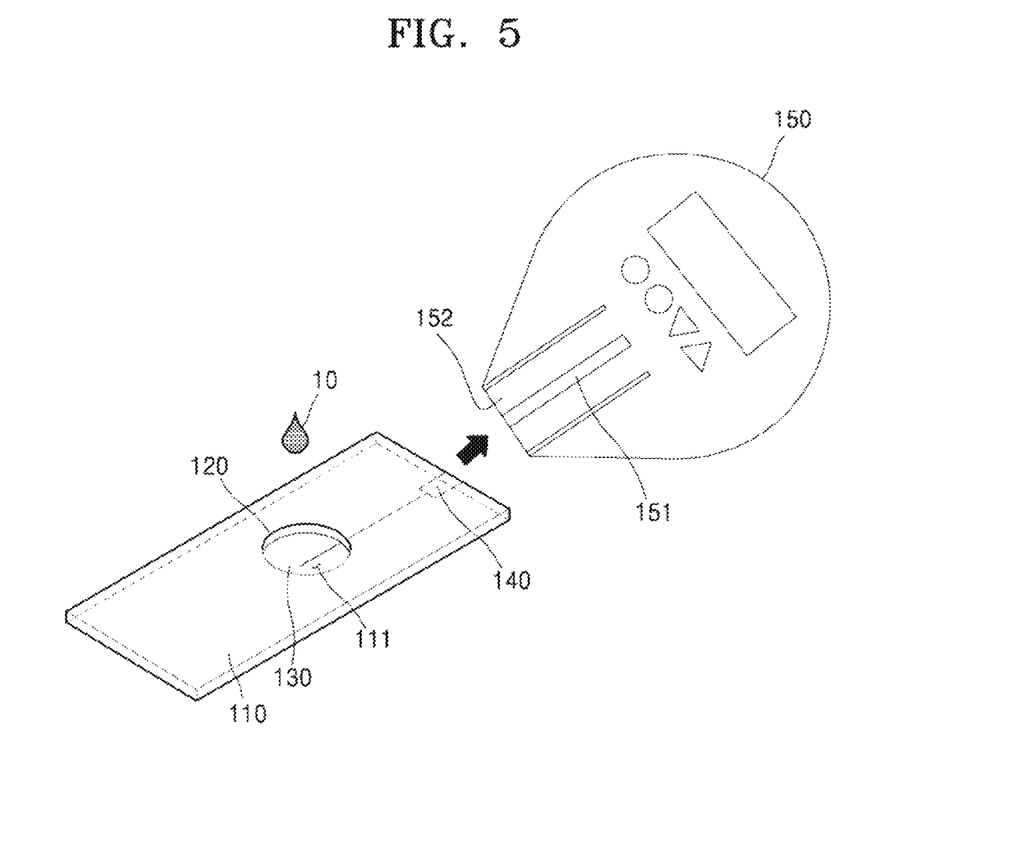
FIG. 5 is a view of a strip and a measuring device according to an embodiment.

Referring to FIG. 5, a strip structure for measuring potassium ions according to an embodiment may further include the measuring device 150 that may include the reference electrode 151 and an inlet 152 into which the strip 110 may be inserted. The measuring device 150 is separated from the strip 110 and may measure potassium ions by inserting the strip 110 into the inlet 152 of the measuring device 150.

By separating the strip 110 including the first working electrode 140 and the measuring device 150 including the reference electrode 151 and using the strip 110 as a disposable one, a user may easily measure potassium ions in a short time and may easily use the measuring device 150 in a normal home.

(The reference electrode 151 shown in FIG. 2 represents the reference electrode 151 included in the measuring device 150, not in the strip 110. The reference electrode 151 shown in FIG. 2 indicates a position where the reference electrode 151 is arranged when the strip 110 is inserted into the measuring device 150.)

Referring to FIG. 5, the measuring device 150 includes the reference electrode 151, and the reference electrode 151 may include platinum (Pt) or silver chloride (AgCl). The inlet 152 of the measuring device 150, which is a hole for inserting the strip 110 into the measuring device 150, may be formed in a shape corresponding to the shape of the strip 110.

When the strip 110 is inserted into the measuring device 150 through the inlet 152, the reference electrode 151 may be inserted into the inner space 111. Here, the reference electrode 151 is arranged outside the potassium ion selective membrane 130.

That is, the first working electrode 140 is arranged inside the potassium ion selective membrane 130, and the reference electrode 151 is arranged outside the potassium ion selective membrane 130. Since the solution 10 inside passes through the potassium ion selective membrane 130, a difference in the concentration of potassium ions occurs between the inside and the outside. The concentration of potassium ions in the solution 10 may be measured by measuring a voltage difference V caused by the concentration difference through the reference electrode 151 and the first working electrode 140.

Figure 6:
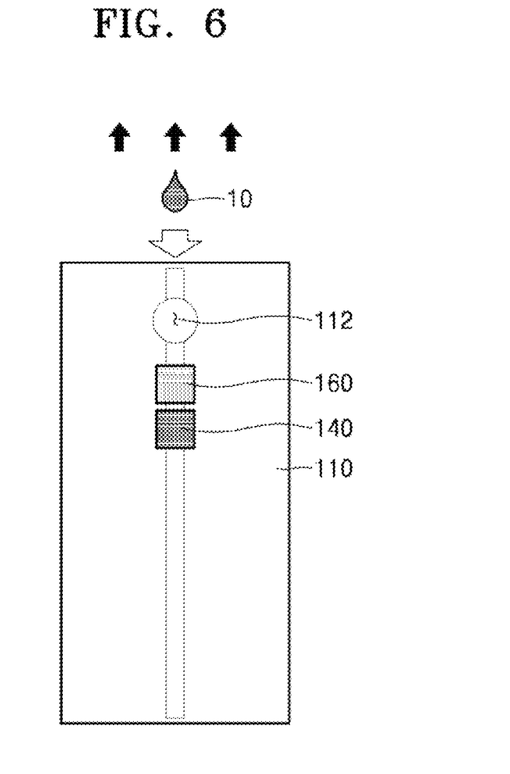
FIG. 6 is a plan view of a strip according to another embodiment.
Figure 7:
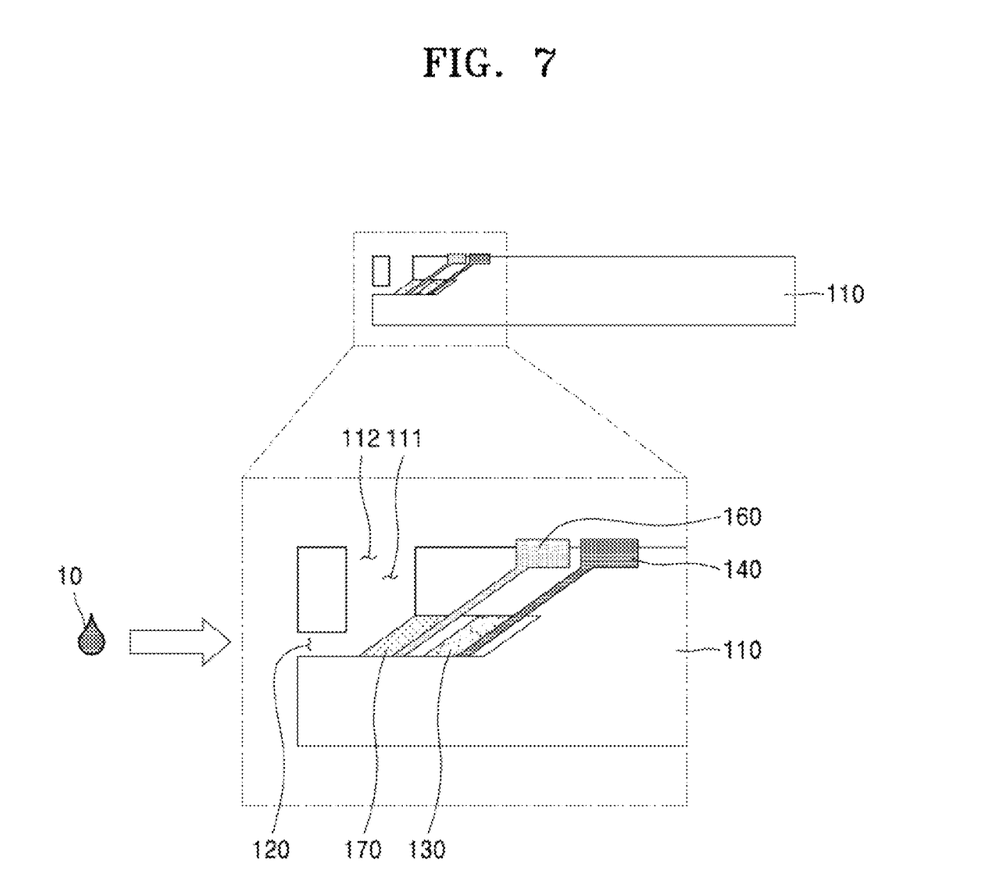
FIG. 7 is an internal cross-sectional view of a strip according to another embodiment.

According to another embodiment, the inlet 120 may be formed on a side surface of the strip 110. Referring to FIGS. 6 and 7, the inlet 120 may be formed on the side surface of the strip 110, not on an upper surface thereof. The inlet 120 may include a capillary (thin tube) having a diameter less than a diameter of the inner space 111, and a capillary phenomenon may be used.

In more detail, when the solution 10 is injected into the inlet 120, even a small amount of the solution 10 may be easily injected into the inlet 120 by the capillary phenomenon. The inlet 120 may be formed of a plurality of capillaries, and the inlet 120 may be formed of porous (including the plurality of capillaries) holes.

According to another embodiment, the first working electrode 140 may extend obliquely with respect to a direction in which the strip 110 extends in a longitudinal direction. The first working electrode 140 may extend in a direction parallel to the longitudinal direction of the strip 110 as shown in FIG. 3. However, as shown in FIG. 7, it is preferable that the first working electrode 140 extends upward and obliquely with respect to the direction in which the strip 110 extends in a longitudinal direction. (Here, the longitudinal direction of the strip 110 may be a horizontal direction in the strip 110 in a plate shape, and a vertical direction may be a width direction.)

As such, extending the first working electrode 140 obliquely with respect to the direction in which the strip 110 extends in a longitudinal direction is to form the potassium ion selective membrane 130 which may be arranged on the first working electrode 140. The potassium ion selective membrane 130 may be arranged on the first working electrode 140 in the form of a solution and then dried.

When the first working electrode 140 is arranged only in a direction parallel to the longitudinal direction of the strip 110, the potassium ion selective membrane 130 in the form of a solution continues to flow along the first working electrode 140 so that the potassium ion selective membrane 130 may not be formed exactly at a desired position.

However, when the first working electrode 140 extends upward and obliquely with respect to the direction in which the strip 110 extends in a longitudinal direction as shown in FIG. 7, a clogging space may be formed through the first working electrode 140. This allows the potassium ion selective membrane 130 in the form of a solution to be dried without flowing, and the potassium ion selective membrane 130 may be accurately positioned at a desired position.

A strip structure for measuring potassium ions according to another embodiment may further include a blood filter membrane 170 in the inner space 111 and capable of removing foreign matter of the solution 10, wherein one side of an electrode extending in a strip shape may be arranged inside the blood filter membrane 170 and the other side of the electrode may further include a second working electrode 160 arranged on a surface of the strip 110.

Referring to FIG. 7, the blood filter membrane 170 is arranged outside the potassium ion selective membrane 130 so that the blood filter membrane 170 may filter large-sized substances such as leukocytes, red blood cells, and the like in the blood before the potassium ion selective membrane 130 filters the solution 10.

When the solution 10 has large-sized substances, the efficiency of selectively passing potassium ions through the potassium ion selective membrane 130 is reduced. In order to prevent such a problem, the blood filter membrane 170 filters the solution 10 first, thereby measuring a more accurate concentration of potassium ions.

The fact that the blood filter membrane 170 is arranged outside the potassium ion selective membrane 130 means that the blood filter membrane 170 may be arranged between the inlet 120 and the potassium ion selective membrane 130. As a result, the blood filter membrane 170 is arranged closer to the inlet 120 than the potassium ion selective membrane 130 so that the blood filter membrane 170 may filter the solution 10 first.

One end of the second working electrode 160 extending in a strip shape is inside the blood filter membrane 170 and the other end is in the surface of the strip 110. In more detail, the second working electrode 160 may be between the blood filter membrane 170 and the potassium ion selective membrane 130 and may be provided to measure other specific materials after filtering the solution 10 into the blood filter membrane 170. In more detail, the second working electrode 160 may measure a substance that may pass through the blood filter membrane 170.

The measuring device 150 may be used to measure other specific materials through the second working electrode 160 and other specific materials may be measured while the strip 110 is inserted into the measuring device 150. (Here, a separate second reference electrode may be included in the measuring device 150.) Therefore, the second working electrode 160 needs to be exposed to the outside of the strip 110 in the same manner as the first working electrode 140 so that the other side of the second working electrode 160 is preferably in the surface of the strip 110.

Referring to FIG. 7, it is preferable that the second working electrode 160 extends upward and obliquely with respect to the direction in which the strip 110 extends in a longitudinal direction in the same manner as the first working electrode 140. This is for forming the blood filter membrane 170 which may be on the second working electrode 160.

The blood filter membrane 170 may be arranged on the second working electrode 160 in the form of a solution and then dried. When the second working electrode 160 is arranged only in a direction parallel to the longitudinal direction of the strip 110, the blood filter membrane 170 in the form of a solution continues to flow along the second working electrode 160 so that the blood filter membrane 170 may not be formed exactly at a desired position.

However, when the second working electrode 160 extends upward and obliquely with respect to the direction in which the strip 110 extends in a longitudinal direction as shown in FIG. 7, a clogging space may be formed through the second working electrode 160. This allows the blood filter membrane 170 in the form of a solution to be dried without flowing, and the blood filter membrane 170 may be accurately positioned at a desired position.

According to an embodiment, the second working electrode 160 may be used to measure other specific materials in the solution 10 and may be omitted if necessary.

According to an embodiment, the strip 110 may include an insertion hole 112 in the surface of the strip 110 and communicating with the inner space 111. The insertion hole 112 is a hole into which the reference electrode 151 of the measuring device 150 may be inserted when the strip 110 is inserted into the measuring device 150, wherein the reference electrode 151 is placed in the inner space 111 through the insertion hole 112. (Here, as described above, the reference electrode 151 may be arranged outside the potassium ion selective membrane 130.)

A strip structure for potassium ion measurement according to the embodiment described above may be operated as follows. First, the solution 10 is inserted into the inner space 111 through the inlet 120. The inlet 120 may be arranged on the upper surface of the strip 110 or may be arranged on a side surface of the strip 110.

The inlet 120 is preferably made of a capillary having a diameter less than the diameter of the inner space 111 and a small amount of the solution 10 may be injected into the inner space 111 by a capillary phenomenon through the inlet 120.

When a sufficient amount of the solution 10 is injected into the inner space 111, potassium ions in the solution 10 pass through the potassium ion selective membrane 130 for a certain period of time, and a difference in the concentration of potassium ions occurs between the inside and the outside of the potassium ion selective membrane 130. (The outside is a direction toward the inlet 120 with the potassium ion selective membrane 130 as a center, and the inside is the opposite direction.)

Thereafter, when the strip 110 is inserted through the inlet 152 of the measuring device 150, the reference electrode 151 of the measuring device 150 is arranged outside the potassium ion selective membrane 130.

The voltage difference V is generated due to a difference in the concentration of potassium ions between an inner side and an outer side of the potassium ion selective membrane 130. The reference electrode 151 arranged outside the potassium ion selective membrane 130 and the first working electrode 140 arranged inside the potassium ion selective membrane 130 may detect the concentration of potassium ions by measuring the voltage difference V.

The strip structure for potassium ion measurement according to the embodiment described above may be modified and used as follows.

Figure 8:
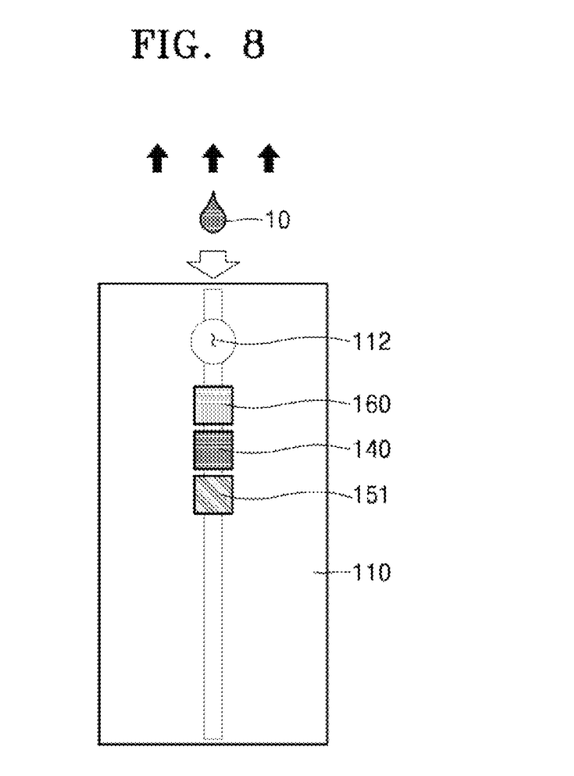
FIG. 8 is a plan view of a strip when a reference electrode is included in the strip according to another embodiment.
Figure 9:
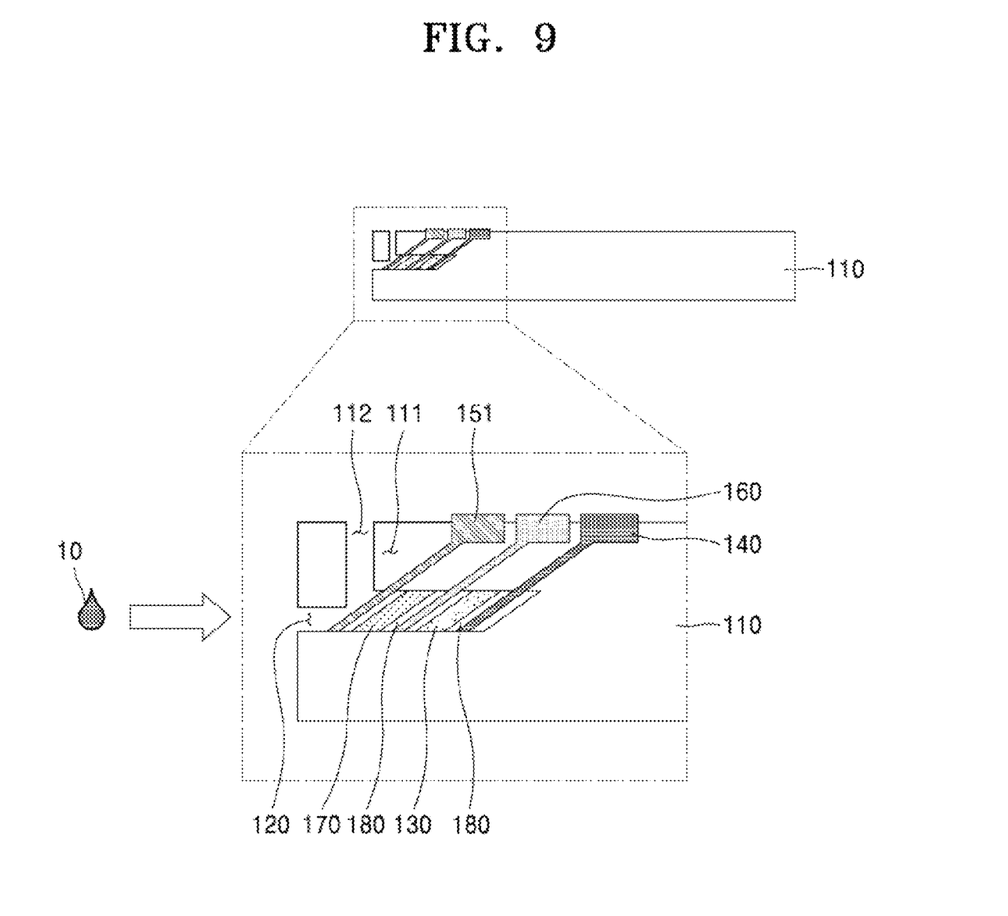
FIG. 9 is an internal cross-sectional view of a strip when a reference electrode is included in the strip according to another embodiment.

Referring to FIGS. 8 and 9, the reference electrode 151 included in the measuring device 150 may be included in the strip 110. That is, the reference electrode 151 may be included in the measuring device 150 or may be included in the strip 110.

In more detail, according to another embodiment, as shown in FIGS. 8 and 9, the reference electrode 151 may be formed on the strip 110 instead of the measuring device 150. The reference electrode 151 extends in a strip shape, and one side of the reference electrode 151 is arranged outside the potassium ion selective membrane 130 and the other side of the reference electrode 151 is in the surface of the strip 110.

In this case, the reference electrode 151 is not included in the measuring device 150, and only a device capable of measuring the potential (V) is formed in the measuring device 150.

One side of the reference electrode 151 may be arranged on the outer side of the potassium ion selective membrane 130 and further on the outermost side of the potassium ion selective membrane 130. When the second working electrode 160 and the blood filter membrane 170 are used, the reference electrode 151 may be arranged outside the second working electrode 160 and the blood filter membrane 170.

When the reference electrode 151 is included in the strip 110, the reference electrode 151 also needs to be exposed to the outside of the strip 110 in the same manner as the first working electrode 140 and the second working electrode 160. Therefore, the other side of the reference electrode 151 is preferably arranged in the surface of the strip 110. Furthermore, referring to FIGS. 8 and 9, it is also preferable that the reference electrode 151 extends upward and obliquely with respect to the direction in which the strip 110 extends in a longitudinal direction.

The reference electrode 151 may be formed by depositing a material that can be used as the reference electrode 151 such as silver chloride (AgCl) according to the shape of the strip 110. A method of inserting the strip 110 after forming the reference electrode 151 using an Ag film is also possible.

Referring to FIG. 9, a gap between the first working electrode 140 and the potassium ion selective membrane 130 of the strip structure for measuring potassium ions according to the embodiment may be filled with an electrolytic material 180 which dissociates into ions and causes a current to flow. In more detail, the electrolytic material 180 may be in a solution state or a gel state, and the electrolytic material 180 may be a hydrogel. (The electrolytic material 180 is not limited to the hydrogel, and various materials may be used as long as they dissociate into ions and cause a current to flow.)

By filling the gap between the first working electrode 140 and the potassium ion selective membrane 130 with the electrolytic material 180 as described above, the accuracy of sensing potassium ions in the blood is increased. Accordingly, the potassium ions in the blood may be accurately measured. Furthermore, referring to FIG. 9, a gap between the second working electrode 160 and the blood filter membrane 170 may also be filled with the electrolytic material 180 which dissociates into ions and causes a current to flow.

Figure 10:
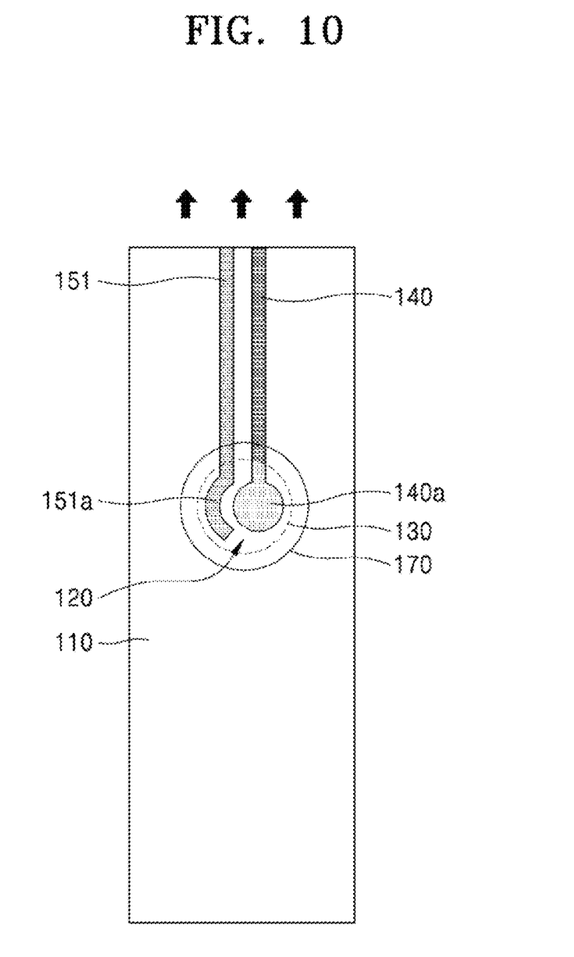
FIG. 10 is a view of a first working electrode contact portion and a reference electrode contact portion according to another embodiment.

Referring to FIG. 10, a strip structure for measuring potassium ions according to an embodiment may be modified and used as follows. The first working electrode 140 and the reference electrode 151 may be formed at the inlet 120 of the strip 110 with a first working electrode contact portion 140a and a reference electrode contact portion 151a having a surface area greater than the width of the first working electrode 140 and the reference electrode 151 having a strip shape.

The first working electrode contact portion 140a and the reference electrode contact portion 151a may be formed through a metal deposition method. When the first working electrode contact portion 140a and the reference electrode contact portion 151a are formed, a contact area between the solution 10 injected through the inlet 120 and the first working electrode 140 and the reference electrode 151 may be widened.

The first working electrode contact portion 140a and the reference electrode contact portion 151a may be formed in various shapes as long as the contact area of the solution 10 with the first working electrode 140 and the reference electrode 151 may be widened.

For example, the first working electrode contact portion 140a may have a circular shape at the inlet 120 and the reference electrode contact portion 151a may have an eyebrow shape. However, the present disclosure is not limited thereto.

As shown in FIG. 10, when the first working electrode contact portion 140a and the reference electrode contact portion 151a are formed in the first working electrode 140 and the reference electrode 151, the first working electrode 140 and the reference electrode 151 may be stacked and arranged on the strip 110.

For example, the reference electrode contact portion 151a, the first working electrode contact portion 140a, the potassium ion selective membrane 130, and the blood filter membrane 170 may be stacked and arranged on the inlet 120. The reference electrode contact portion 151a is arranged in the inlet 120 and the blood filter membrane 170 is arranged under the reference electrode contact portion 151a. The potassium ion selective membrane 130 may be arranged under the blood filter membrane 170 and the first working electrode contact portion 140a may be arranged under the potassium ion selective membrane 130.

That is, according to another embodiment, when the first working electrode 140 and the reference electrode 151 are stacked and arranged on the strip 110, the reference electrode contact portion 151a, the blood filter membrane 170, the potassium ion selective membrane 130, and the first working electrode contact portion 140a may be stacked and arranged on the inlet 120.

Thus, foreign matter of blood may be removed through the blood filter membrane 170 while widening the contact area of the solution 10 with the first working electrode 140 and the reference electrode 151, and the potassium concentration of the blood may be measured through the reference electrode 151—the potassium ion selective membrane 130—the first working electrode 140.

The strip structure for potassium ion measurement according to the embodiment described above has the following effects.

Conventionally, in order to measure the potassium concentration in the body, it takes a lot of time to visit a hospital or a medical examination center to conduct a blood test, an electrocardiogram examination, and the like. However, the strip structure for measuring potassium ions according to the embodiment of the present disclosure may easily measure the potassium concentration in the body any time through the measuring device 150 capable of measuring a voltage and the strip 110 used as a disposable.

In more detail, according to the strip structure for measuring potassium ions according to the embodiment of the present disclosure, a user may easily measure the potassium concentration at home without visiting the hospital or the medical examination center by separating the strip 110 including the first working electrode 140 and the measuring device 150 including the reference electrode 151 and by using the strip 110 as a disposable.

Furthermore, in the past, since the blood test and the electrocardiogram examination have been performed to measure the potassium concentration in the body, the examination procedure is complicated and time-consuming. However, the strip structure for measuring potassium ions according to the embodiment of the present disclosure has an advantage that the potassium ions in the body may be simply measured by dropping the solution 10 on the strip 110 using the potassium ion selective membrane 130 and the first working electrode 140.

Furthermore, the conventional device for measuring potassium concentration in the body is difficult to carry and use at home because it is large. However, the strip structure for measuring potassium ions according to the embodiment of the present invention is compatible with the strip 110 which may be used as a disposable, and thus the measuring device 150 capable of measuring voltage may be manufactured in a small size and may be easily used.

This allows a patient who needs to constantly manage the potassium concentration in the body to monitor the potassium concentration any time while measuring the potassium concentration at home quickly and easily.

According to the strip structure for measuring potassium ions according to one or more embodiments, the concentration of potassium in the body may be easily measured at all times through a measuring device capable of measuring voltage and a disposable strip, and the concentration of potassium in the body may also be easily measured by a method for dropping a solution on a strip using a potassium ion selective membrane and a first working electrode.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A strip structure for measuring potassium ions, the strip structure comprising:
   a strip having an inner space for receiving a solution therein and being formed in a plate shape;
   an inlet formed in the strip and capable of injecting a solution into the inner space of the strip;
   a potassium ion selective membrane arranged in the inner space and capable of permeating potassium ions of the solution;
   a blood filter membrane arranged in the inner space and capable of removing foreign matter of the solution;
   a first working electrode extending in a strip shape, wherein one side of the first working electrode is arranged inside the potassium ion selective membrane and the other side of the first working electrode is on a surface of the strip,
   wherein the blood filter membrane is arranged between the inlet and the potassium ion selective membrane; and
   a second working electrode extending in a strip shape, wherein one side of the second working electrode is arranged inside the potassium ion selective membrane and the other side of the second working electrode is in the surface of the strip, wherein one side of the second working electrode is between the blood filter membrane and the potassium ion selective membrane.

2. The strip structure of claim 1, further comprising:
   a measuring device comprising a reference electrode and an inlet into which the strip is inserted,
   wherein the measuring device is separated from the strip and measures potassium ions by inserting the strip into the inlet of the measuring device.

3. The strip structure of claim 1, wherein the second working electrode extends upward and obliquely with respect to a direction in which the strip extends in a longitudinal direction.

4. The strip structure of claim 1, wherein the inlet comprises a capillary having a diameter less than a diameter of the inner space.

5. The strip structure of claim 4, wherein the inlet comprises a plurality of capillaries.

6. The strip structure of claim 1, wherein the potassium ion selective membrane comprises cellulose acetate.

7. The strip structure of claim 2, wherein the strip comprises an insertion hole arranged in the surface of the strip and communicating with the inner space, and
   the reference electrode of the measuring device is inserted into the insertion hole when the strip is inserted into the measuring device.

8. The strip structure of claim 1, further comprising:
   a reference electrode extending in a strip shape, wherein one side of the reference electrode is arranged outside the potassium ion selective membrane and the other side of the reference electrode is in the surface of the strip.

9. The strip structure of claim 1, wherein a gap between the first working electrode and the potassium ion selective membrane is filled with an electrolytic material.

* * * * *